United States Patent [19]

Dale et al.

[11] 3,997,563
[45] Dec. 14, 1976

[54] PROCESS FOR SELECTIVE PREPARATION OF MACROCYCLIC POLYETHERS

[75] Inventors: Johannes Dale, Bloomenholm; Kari Daasvatn, Saetre, both of Norway

[73] Assignee: Johannes Dale, Norway

[22] Filed: May 27, 1975

[21] Appl. No.: 580,794

[30] Foreign Application Priority Data

May 28, 1974 Norway .............................. 1930/74

[52] U.S. Cl. .............................................. 260/338
[51] Int. Cl.² ..................................... C07D 323/00
[58] Field of Search .................................. 260/338

[56] References Cited

OTHER PUBLICATIONS

J. Dale et al., Acta. Chem. Scand., Ser. B (1974), 28(3) pp. 378–379.

*Primary Examiner*—Norma S. Milestone
*Attorney, Agent, or Firm*—Wenderoth, Lind & Ponack

[57] ABSTRACT

Cyclic polyethers of the general formula

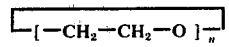

in which n is an integer from 3 – 11, particularly from 4 – 6, are prepared by oligomerization of ethylene oxide in the presence of boron trifluoride, phosphorus pentafluoride or antimony pentafluoride as catalyst, and in the presence of fluoborate, fluophosphate or fluoantimonate salts of alkali metals, alkaline earth metals or transition metals, to form complexes between the polyethers formed and said salts, separating the complexes from the reaction mixture and liberating the polyethers from the complexes.

6 Claims, No Drawings

PROCESS FOR SELECTIVE PREPARATION OF MACROCYCLIC POLYETHERS

This invention relates to a process for preparing macrocyclic polyethers.

In our copending application 430.510 there is described a process for preparing cyclic polyethers of the general formula

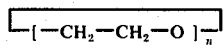

in which $n$ is an integer, by oligomerization of ethylene oxide in the presence of boron trifluoride, phosphorus pentafluoride or antimony pentafluoride as catalyst, optionally with hydrogen fluoride as cocatalyst, with strict exclusion of compounds which can provide terminal groups for the formation of linear polymers.

The proportion of the polyethers prepared (i.e. compounds of the above formula with different values of n) seems to a great extent to be determined by the catalyst and is essentially not influenced by variation in temperature, solvent and concentration. The majority of the formed product is dioxan, but satisfactory methods for the preparation thereof are previously known. The larger rings which are formed, do not only comprise those rings which are of the greatest interest with respect to complex-formation with cations. The polyethers of the above formula which are of particular interest for this purpose, are those in which $n = 4, 5$ and 6, and it is therefore desirable to be able to control the ring-formation so that only or primarily the complexing rings are formed.

We have now found that the desired cyclic polyethers can be prepared selectively or essentially selectively by carrying out the above oligomerization in the presence of certain salts containing cations of the type which forms complexes with the polyethers formed, whereafter the complexes are separated off, and the polyethers are liberated therefrom.

A series of conditions must be fulfilled for such a process to be carried out, and it is not at all obvious how this should be attained in practice:

Condition 1. The ether formation itself must be reversible.

Condition 2. The salt must not inactivate the catalyst.

Condition 3. The salt must not provide potential terminal groups for formation of linear polymers.

Condition 4. It must be easy to liberate the cyclic ethers from the complex.

The problems encountered are briefly described in the following:

Condition 1. There has not been described any catalyst which is active for isomerization of stable ethers at the low temperatures (20°–30° C) at which the oligomerization takes place. We have also found experimentally that the cyclic tetramer of ethylene oxide is completely stable in the presence of $BF_3$ or $HF/BF_3$ at 160° C for 24 hours. However, in the presence of ethylene oxide an isomerization takes place rapidly. This means that the actual catalyst is an oxonium salt which is formed due to the fact that ethylene oxide acts as an alkylating agent in the presence of $BF_3$ and the like. Our experiments have therefore shown that during the oligomerization process a reversibility is present, which could not be predicted.

Condition 2. Most of the common salts contain anions which will react with $BF_3$ and corresponding Lewis acids with the formation of complex anions. The system will thereby become neutral and the reaction stops. This does not only apply to fluorides, which obviously form fluoborates, fluophosphates etc., but also to other common anions. Thus, an effort to oligomerize 57 g of ethylene oxide in the presence of 0.05 g of $BF_3$ and 2 g of KF in 25 ml of dioxan for 18 hours resulted in a yield of cyclic oligomers of only 0.2 g and with normal distribution with respect to ring size (see example 1). Similarly an effort to oligomerize 34 g of ethylene oxide in the presence of 0.05 g of $BF_3$ and 2 g of $K_2SO_4$ in 25 ml of dioxan for 18 hours resulted in a yield of only 0.2 g of cyclic ethers.

Condition 3. Ordinary salts have a considerable tendency to enter into a nucleophilic substitution and will therefore possibly block a chain end and prevent cyclisation.

Condition 4. It must be borne in mind that complexes of ordinary salts are readily soluble, since one of the fields of use of cyclic ethers is specifically to render inorganic salts soluble in organic solvents.

Condition 5. The simplest way to liberate the cyclic ethers from the complexes will in principle be removal of the volatile ethers from the non-volatile salt by distillation. However, another field of use of the cyclic ethers is that the anion of the salt is separated from the cation ("naked anion"), and thereby an extreme activation as nucleophilic agent and base is obtained. As expected, it is found that heating of ether complexes of ordinary salts, alkalimetal halides, -p-toluene sulphonates, etc., results in a complete destruction of the ethers, and they must therefore be liberated in a laborious manner, for instance filtration through an alumina column with a carefully adjusted mixture of eluants (J. Dale and P. O. Kristiansen, Acta Chem. Scand. 26 1471 (1972)).

Our experiments have now shown that the only types of salts which satisfy all the conditions, are fluoborate, fluophosphate or fluoantimonate salts, preferably of alkali metals, but also of alkaline earth metals and transition metals. These are maintained in suspension during the oligomerization process and are gradually dissolved, while the complexes formed are gradually precipitated with the rings of interest, as crystals or a non-crystalline separate phase. The equilibrium in the solution is thereby displaced as long as ethylene oxide and active catalyst are present, and the entire process is thereby controlled so that only the complexing rings are formed.

The precipitated complex is removed by filtration, and since it is not necessary to neutralize the catalyst, the mother liquor which contains larger or smaller amounts of ethers which have not formed complexes, may be used further by adding more ethylene oxide and more salt thereto. The complexed polyethers are then liberated either by direct heating of the complexes or by means of a solvent or a mixture of solvents which exhibit good solubility for the polyether and insolubility for the salt, and the polyether is then isolated by evaporation of the solvent. The salt which remains after liberation of the polyether, can then be recycled to the process.

When selecting a salt it must primarily be taken into consideration that the cation must have a strong tendency to form complexes with the desired rings and be able to withstand heating. Both these requirements render the alkali metal salts most suitable, while they at the same time are also easily available in anhydrous form. Lithium salts lead to the formation of a mixture of tetramer and pentamer; sodium leads to the formation of tetra-, penta- and hexamer; and potassium leads to the formation of pentamer and hexamer. Rubidium and cesium primarily lead to the formation of hexamer. The less readily available anhydrous flouborates, fluophosphates and fluoantimonates of alkaline earth metals and transition metals lead to the formation of the same rings with a distribution which can be expected in view of their ionic radius.

The product distribution is affected only to a minor extent by the nature of the anion. The larger anions ($PF_6^-$, $SbF_6^-$) promote the formation of somewhat smaller rings than when the smaller anion ($BF_4^-$) is employed, presumably due to the fact that the cation will more readily form 2:1 complexes of sandwich type with the smaller rings when the anion is large. With the larger rings the stoechiometric ratio in the complexes is usually 1:1. It has also been observed that the crystalline fluoborate complexes usually contain loosely bonded dioxan (dioxan alone does not give any complex formation), while the crystalline fluophosphate complexes do not contain dioxan. It is practical, but not necessary, that the anion corresponds to the employed catalyst.

Comparative experiments have shown that it is not necessary with HF as cocatalyst when the oligomerization is performed in the presence of salts.

The amount of salt to be added is determined by practical considerations. The use of stoechiometric amounts relative to the amount of the ethylene oxide introduced may have the effect that the entire mixture solidifies to a solid mass which is difficult to handle, and it is therefore preferable to use less salt, such as 50 per cent of the stoechiometrically required amount and to recycle non-complexed product.

For the preparation of polyethers having a specific ring size in pure condition, it is possible either to fractionate the mixture of complexes by recrystallization before liberating the polyethers, or to fractionate the liberated mixture of polyethers by distillation.

The following examples are given to illustrate the invention further.

FIRST GROUP OF EXAMPLES

These examples are intended to illustrate the effect of the salt addition according to the invention with the use of relatively small amounts of salt. The reactions were carried out by first suspending the stated amount of salt in dry dioxan under a dry nitrogen atmosphere. When $BF_3$ was employed as catalyst, it was added in the form of a standard solution prepared by absorption of 3.8 g of $BF_3$ in 50 ml of dry dioxan at 5° C, and accordingly it contained 0.07 g of $BF_3$ per ml. Corresponding standard solutions in dioxan were also prepared when the catalyst was $PF_5$ or $SbF_5$. The stated amount of cooled ethylene oxide was then added slowly (to prevent temperature rise) to the ice-cooled mixture, and the entire blend was stirred well for 6 hours. After additional 12 hours of stirring at 20° C the reaction mixture was filtered, and the filtrate was neutralized with $NH_3$ gas and evaporated in a rotating evaporator. The solid material which had been filtered off, was washed with dioxan saturated with $NH_3$. Both fractions were then analysed with respect to ring composition by means of gas chromatography.

EXAMPLE 1

1.5 g $LiBF_4$, 25 ml dioxan, 0.07 g $BF_3$ and 71 g ethylene oxide. The precipitated crystalline material weighed 5.1 g and was found to be a pure pentamer complex (m.p. 170° C). The cyclic ether was isolated by pyrolysis at 160° C/0.002 mm Hg. The evaporation residue from the filtrate was a viscous liquid and weighed 15 g. In addition to some unevaporated dioxan the mixture contained the higher cyclic ethers with $n =$ 3,4,5,6,7,8,9 in the ratio 2:10:6:8:6: 2:1, which shows that the ratio between the cyclic ethers in the filtrate does not differ essentially from that which is observed without addition of salt (herein called "normal distribution").

EXAMPLE 2

1.7 g $NaBF_4$, 25 ml dioxan, 0.07 g $BF_3$ and 62 g ethylene oxide. The precipitated crystalline material weighed 5.8 g and contained dioxan, tetramer, pentamer and hexamer in the ratio 1:2:1:2. The evaporation residue from the filtrate weighed 10 g and contained in addition to some unevaporated dioxan all the cyclic oligomers, but with some more pentamer and less hexamer than corresponding to the normal distribution.

EXAMPLE 3

2.0 g $KBF_4$, 25 ml dioxan, 0.05 g $BF_3$ and 48 g ethylene oxide. The precipitated complex weighed 6.2 g and contained pentamer and hexamer in the ratio 1:4. The residue after evaporation of the filtrate weighed 10 g and contained less hexamer than corresponding to the normal distribution.

EXAMPLE 4

1.4 g $RbBF_4$, 25 g dioxan, 0.05 g $BF_3$ and 68 g ethylene oxide. The precipitated complex weighed 2.5 g and was found to contain hexamer only. The residue after evaporation of the filtrate weighed 16.6 g and contained the cyclic oligomers in normal distribution. Pyrolysis of 2.1 g of the above complex at max. 200° C/0.02 mm Hg yielded 0.9 g cyclic hexamer.

EXAMPLE 5

2.5 g $CsBF_4$, 12 ml dioxan, 0.03 g $BF_3$ and 26 g ethylene oxide. The precipitated complex weighed 2.5 g and contained hexamer only. The residue after evaporation of the filtrate weighed 7.4 g and contained the cyclic oligomers in normal distribution. Pyrolysis of 2.3 g of the above complex at max. 200° C/0.02 mm Hg yielded 1.0 g cyclic hexamer.

EXAMPLE 6

6.0 g anhydrous $Ca(BF_4)_2$, prepared from $CaF_2$ and $BF_3$ etherate (de Pape and Ravez, Compt. rend. 254, 4171 (1962)), 35 ml dioxan, 0.05 g $BF_3$ and 68 g ethylene oxide. The precipitated complex weighed 15.5 g and contained tetramer and pentamer in the ratio 1:1. The residue after evaporation of the filtrate weighed 15 g and contained the cyclic oligomers with some more pentamer than corresponding to normal distribution. Upon standing 0.5 g of the complex which contained only the hexamer crystallized out.

EXAMPLE 7

11.5 g anhydrous $Sr(BF_4)_2$, crystallized with dioxan, 50 ml dioxan, 0.07 g $BF_3$ and 108 g ethylene oxide. The precipitated complex weighed 19 g and contained tetramer, pentamer and hexamer in the ratio 1:6:6. The residue after evaporation of the filtrate weighed 40 g and contained a larger proportion of pentamer than corresponding to normal distribution.

EXAMPLE 8

16.0 g anhydrous $Ba(BF_4)_2$, crystallized with dioxan, 50 ml dioxan, 0.07 g $BF_3$ and 101 g ethylene oxide. The precipitated complex weighed 19 g and contained tetramer, pentamer and hexamer in the ratio 1:3:7. The residue after evaporation of the filtrate weighed 40 g and contained the cyclic oligomers in normal distribution.

EXAMPLE 9

4.0 g anhydrous $AgBF_4$, 35 ml dioxan, 0.07 g $BF_4$ and 95 g ethylene oxide. The precipitated crystalline complex weighed 5 g and contained hexamer only. After separating off a non-crystalline viscous phase the filtrate was evaporated to give a residue weighing 14.3 g. Upon standing a total of 8.5 g of a complex containing tetramer and pentamer in the ratio 4:3 was crystallized from these fractions. The remaining filtrate fraction contained particularly little of the hexamer in comparison with the normal distribution of cyclic oligomers.

EXAMPLE 10

23.5 g anhydrous $Hg(BF_4)_2$, crystallized with dioxan, 50 ml dioxan, 0.07 g $BF_3$ and 120 g ethylene oxide. The precipitated crystalline complex weighed 6 g and contained tetramer, pentamer and hexamer in the ratio 14:2:1. The filtrate separated in an upper phase (43 g) containing cyclic oligomers with a major amount of pentamer, and a lower phase (33 g) with larger amounts of pentamer and hexamer than corresponding to a normal distribution.

EXAMPLE 11

$Ni(BF_4)_2$ hydrate was made anhydrous by slurrying it in dioxan and distilling off a water-dioxan azeotrope in vacuum, and the $Ni(BF_4)_2$dioxanate was used directly. 7 g of $Ni(BF_4)_2$ dioxanate, 50 ml dioxan, 1 g $BF_3$ and 63 g ethylene oxide. The product separated in a lower, green phase and an upper, colourless phase. The lower phase weighed 38 g and contained dioxan and pentamer in the ratio 3:1, and small amounts of tetramer and hexamer. After evaporation the upper phase weighed 37.5 g and contained all the cyclic oligomers but with particularly much pentamer in comparison with the normal distribution (pentamer and tetramer in the ratio 3:1).

EXAMPLE 12

$Cu(BF_4)_2$ hydrate was converted to dioxanate by azeotropic distillation with dioxan. 15 g of $Cu(BF_4)_2$ dioxanate, 50 ml of dioxan, 1 g of $BF_3$ and 67 g of ethylene oxide. The blue slurry gradually separated in a homogeneous green, lower phase and a homogeneous colourless, upper phase. The lower phase weighed 69 g and contained dioxan and pentamer in the ratio 3:1, and small amounts of tetramer and hexamer. After evaporation the upper phase weighed 11 g and contained the cyclic oligomers in normal distribution.

EXAMPLE 13

$Zn(BF_4)_2$ hydrate was converted to dioxanate by azeotropic distillation with dioxan. 15 g $Zn(BF_4)_2$ dioxanate, 50 ml of dioxan, 1 g of $BF_3$ and 68 g of ethylene oxide. The product separated in two homogeneous phases. The lower phase weighed 73 g and contained dioxan and pentamer in the ratio 3:1 and small amounts of tetramer and hexamer. After evaporation the upper phase weighed 30 g and contained the cyclic oligomers in normal distribution.

EXAMPLE 14

3.5 g of $KPF_6$, 25 ml of dioxan, 0.05 g of $BF_3$ and 50 g of ethylene oxide. The precipitated complex weighed 4.7 g and contained tetramer, pentamer and hexamer in the ratio 1:8:4. The residue after evaporation of the filtrate weighed 3 g and contained the cyclic oligomers in normal distribution.

EXAMPLE 15

8.0 g of $KPF_6$, 25 ml of dioxan., 0.1 g of $PF_5$ and 92 g of ethylene oxide. The product separated in two phases which were evaporated separately. The lower phase became semicrystalline and weighed 25.3 g, and it contained primarily dioxan, tetramer, pentamer and hexamer in the ratio 1:1:2:2. The upper phase gave a residue after evaporation weighing 2 g and contained the cyclic oligomers in normal distribution.

EXAMPLE 16

12.0 g of $KSbF_6$, 25 ml of dioxan, 0.3 g of $SbF_5$ and 104 g ethylene oxide. The precipitated crystalline complex weighed 21.5 g and contained pentamer only. The filtrate separated in two phases. After evaporation the lower phase weighed 9 g and contained tetramer, pentamer and hexamer in the ratio 2:1:2. After evaporation the upper phase weighed 6.5 g and contained the cyclic oligomers in normal distribution with some contamination of unknown by-products.

SECOND GROUP OF EXAMPLES

The examples of this group illustrate experiments carried out under the same conditions as in the first group of examples, with the exception that larger amounts of salt were used for preparative reaction.

EXAMPLE 17

10.4 g of $LiBF_4$, 10 ml of dioxan, 0.07 g of $BF_3$ and 54 g of ethylene oxide. The product separated in two liquid phases which were processed separately. After evaporation the lower phase weighed 57 g and contained tetramer and pentamer in the ratio 1:2 and residues of unevaporated dioxan. After evaporation the upper phase weighed 2 g and contained the cyclic oligomers with a larger amount of pentamer than corresponding to normal distribution.

EXAMPLE 18

61 g of $NaBF_4$, 100 ml of dioxan, 0.2 g of $BF_3$ and 193 g of ethylene oxide. The product was a viscous crystal broth. After lenient drying the solid material filtered off weighed 195 g and contained dioxan, tetramer, pentamer and hexamer in the ratio 4:1:2:1. After evaporation the filtrate weighed 14.5 g and contained the cyclic oligomers with a higher content of pentamer than corresponding to a normal distribution.

From the solid complex mixture the cyclic oligomers were liberated by thermal decomposition. At 20° C/10 mm Hg 55 g of dioxan was distilled off. The residue (140 g) was heated at 180° C/0,1 mm Hg. The distillate consisted of 49 g of dioxan, 12 g of tetramer, 24 g of pentamer and 12 g of hexamer. The residue after the pyrolysis consisted of 42 g of NaBF$_4$ as a dry powder which was only slightly discoloured.

Comparative experiments showed that the same result is obtained also if neutralization of catalyst and washing of the crystalline complex are omitted.

EXAMPLE 19

70 g of KBF$_4$, 100 ml dioxan, 0.2 g and 198 g ethylene oxide. The solid material which was filted off, weighed only 78 g and consisted primarily of unreacted KBF$_4$, and it contained dioxan, pentamer and hexamer in the ratio 1:1:1. After evaporation the filtrate weighed 25 g and contained in particular little hexamer relative to the normal distribution.

EXAMPLE 20

20 g of NaBF$_4$, 100 ml of CH$_2$Cl$_2$, 0.07 g of BF$_3$ and 100 g of ethylene oxide. 1.2 g of unreacted salt was filtered off from the reaction product. The solvent was removed from the filtrate by distillation at 760 mm Hg. The distillation residue weighed 106 g and contained primarily dioxan, tetramer, pentamer and hexamer in the ratio 5:4:2:1. From the semicrystalline mass 32 g of dioxan were distilled off at 25° C/10 mm Hg. The crystalline residue yielded upon heating to maximum 240° C/8 mm Hg 42 g of cyclic oligomers, primarily tetramer, pentamer and hexamer. The residue remaining after heating weighed 30 g.

EXAMPLE 21

31 g of NaBF$_4$, 100 ml of benzene, 0.07 g of BF$_3$ and 97 g of ethylene oxide. The product separated in an upper dioxan-rich phase and a lower viscous phase. The entire product was processed further together. Dioxan and minor amounts of unreacted ethylene oxide, 56 g in all, were removed by distillation at 25° C/10 mm Hg. Distillation of the residue at 200° C/0.02 mm Hg yielded 325 g of cyclic oligoethers, primarily tetramer, pentamer and hexamer in the ratio 4:2:1. The residue remaining after the final distillation weighed 39 g.

We claim:
1. Process for preparing cyclic polyethers of the general formula

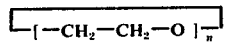

in which n is an integer from 4 to 6, by oligomerization of ethylene oxide in the presence of a catalyst, characterized in that the oligomerization is carried out in a solvent in the presence of a catalyst selected from the group consisting of boron trifluoride, phosphorus pentafluoride and antimony pentafluoride, and in the absence of compounds which can provide potential terminal groups which will lead to the formation of linear polymers, and that the oligomerization is carried out in the presence of salts selected from the group consisting of fluoborate, fluophosphate and fluoantimonate salts of alkali metals, alkaline earth metals and transition metals selected from the group consisting of Ag, Hg, Ni, Cu and Zn, to form complexes between the polyethers formed and said salts, separating the complexes from the reaction mixture and liberating the polyethers from the complexes.

2. Process according to claim 1, characterized in that dioxan is used as a solvent.

3. Process according to claim 1, characterized in that the polyethers are liberated from the complexes by heating.

4. Process according to claim 3, characterized in that the heating is performed in the presence of a solvent.

5. Process according to claim 1, characterized in that the salt remaining after the liberation of the polyethers, is used again for complex formation.

6. Process according to claim 1, characterized in that the mother liquor remaining after the separation of the complexes and containing unreacted ethylene oxide, non-neutralized catalyst and non-complexed cyclic ethers is used again for oligomerization.

* * * * *